United States Patent
Guo et al.

(10) Patent No.: US 11,596,741 B2
(45) Date of Patent: Mar. 7, 2023

(54) ADAPTER MANIFOLD FOR MULTI-BARREL SYRINGE APPLICATOR

(71) Applicant: Ethicon, Inc., Somerville, NJ (US)

(72) Inventors: Jianxin Guo, Livingston, NJ (US); Jared Schneider, Union, NJ (US); Christopher Anthony Kokinelis, Flemington, NJ (US); Jorge Maria Manzano Riera, Sant Cugat del Valles (ES)

(73) Assignee: Ethicon, Inc., Raritan, NJ (US)

( * ) Notice: Subject to any disclaimer, the term of this patent is extended or adjusted under 35 U.S.C. 154(b) by 771 days.

(21) Appl. No.: 15/957,241

(22) Filed: Apr. 19, 2018

(65) Prior Publication Data
US 2019/0321554 A1 Oct. 24, 2019

(51) Int. Cl.
*A61M 5/19* (2006.01)
*A61M 39/10* (2006.01)
(Continued)

(52) U.S. Cl.
CPC .......... *A61M 5/19* (2013.01); *A61M 5/3134* (2013.01); *A61M 5/3294* (2013.01); *A61M 39/10* (2013.01); *A61B 17/00491* (2013.01); *A61B 2017/00495* (2013.01); *A61B 2017/00522* (2013.01); *A61M 2005/3131* (2013.01); *A61M 2039/1077* (2013.01)

(58) Field of Classification Search
CPC .......... A61M 5/19; A61M 2039/0027; A61M 2039/1077; A61M 39/10; A61M 39/105; A61M 5/1407; A61M 5/1408; A61M 5/1413; A61M 5/3134; A61M 5/3294; A61M 2005/3131; A61M 2005/3142; A61B 17/00491; A61B 2017/00495; A61B 2017/00522
See application file for complete search history.

(56) References Cited

U.S. PATENT DOCUMENTS 5,354,284 A 10/1994 Haber et al.
5,582,596 A 12/1996 Fukunaga et al.
(Continued)

FOREIGN PATENT DOCUMENTS

DE 295 16 077 U1 2/1997
EP 2158848 A1 3/2010
(Continued)

OTHER PUBLICATIONS

Notice of Allowance issued in U.S. Appl. No. 29/688,316 dated Oct. 4, 2019, 14 pages.
(Continued)

*Primary Examiner* — Shefali D Patel

(57) ABSTRACT

An adapter manifold having an adapter body and a syringe applicator, wherein the adapter body has substantially parallel inlet ports and substantially parallel exit ports, the inlet ports spaced an axial distance apart which is different from an axial distance between the exit ports, to accommodate the syringe applicator which has multiple substantially parallel syringes, and substantially parallel syringe connectors in fluid communication with the inlet ports having Luer-type receivers on proximal ends thereof, wherein the syringe connectors are biased toward a proximal end of the adapter body.

32 Claims, 5 Drawing Sheets

(51) Int. Cl.
  *A61M 5/31* (2006.01)
  *A61M 5/32* (2006.01)
  *A61B 17/00* (2006.01)

(56) References Cited

U.S. PATENT DOCUMENTS

| | | | |
|---|---|---|---|
| 6,063,055 A * | 5/2000 | Epstein | A61B 17/00491 604/191 |
| 6,461,361 B1 * | 10/2002 | Epstein | A61B 17/00491 222/145.2 |
| 6,874,657 B2 * | 4/2005 | Metzner | A61P 7/04 222/82 |
| D547,447 S | 7/2007 | Bruce et al. | |
| 8,006,953 B2 * | 8/2011 | Bennett | A61M 39/045 251/149.1 |
| D649,240 S | 11/2011 | Lewis et al. | |
| D653,329 S | 1/2012 | Lee-Sepsick | |
| D660,957 S | 5/2012 | Lee-Sepsick | |
| D672,456 S | 12/2012 | Lee-Sepsick | |
| D709,612 S | 7/2014 | Lewis | |
| D747,473 S | 1/2016 | Martin et al. | |
| D748,246 S | 1/2016 | Perthu | |
| D749,721 S | 2/2016 | Dziak et al. | |
| 9,486,190 B2 | 11/2016 | Sherman et al. | |
| D828,918 S | 9/2018 | Eisele | |
| D834,181 S | 11/2018 | Lee-Sepsick | |
| D838,366 S | 1/2019 | Lewis | |
| 10,391,234 B2 | 8/2019 | Sams et al. | |
| 2004/0143219 A1 * | 7/2004 | Lee | A61M 25/09041 604/167.03 |
| 2005/0096588 A1 * | 5/2005 | Hagmann | A61B 17/00491 604/82 |
| 2014/0276567 A1 | 9/2014 | Goodman | |
| 2015/0141928 A1 * | 5/2015 | Laugere | A61M 5/284 604/191 |

FOREIGN PATENT DOCUMENTS

| | | |
|---|---|---|
| WO | 03/039375 A2 | 5/2003 |
| WO | 2017086807 A1 | 5/2017 |

OTHER PUBLICATIONS

Notice of Allowance issued in U.S. Appl. No. 29/688,327 dated Oct. 4, 2019, 14 pages.
Non-Final Office Action issued in U.S. Appl. No. 29/688,286 dated Oct. 17, 2019, 14 pages.
International Search Report for related International Application No. PCT/IB2019/053012, dated Aug. 6, 2019, 5 pages.
Search Report for related European Patent Application No. 21212870.6-1122, dated Apr. 12, 2022, 10 pages.
Summary of the Office Action for related Russian Patent Application No. 2020 137 709, dated Aug. 5, 2022, 1 page.

* cited by examiner

ADAPTER MANIFOLD FOR MULTI-BARREL SYRINGE APPLICATOR

FIELD

Disclosed is an adapter manifold for modifying the flow path from a multi-barrel syringe applicator for multi-component medical sealant materials to a mixing/delivery tip, wherein the syringe applicator has a different axial distance between exit nozzles as compared to the mixing tip.

ENVIRONMENT

In recent years, minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

One example of a common minimally invasive surgery involves laparoscopic surgical procedures. Laparoscopic procedures may be used to treat hernias, colon dysfunctions, gastroesophageal reflux disease, gallbladder disorders, etc. Typically, the patient undergoing the procedures will return home hours after undergoing surgery.

One challenge presented when performing minimally invasive surgical procedures relates to reducing bleeding at a surgical site when control of bleeding by standard surgical techniques, such as suturing, ligature and cautery, is ineffective or impractical. As opposed to conventional surgical procedures, the surgeon's access to the site of the incision is greatly reduced during minimally invasive procedures and conventional techniques for hemostasis may be difficult to effect.

Recently, the use of tissue sealants and other biological adhesive materials has emerged as an alternate technique of sealing incisions. Such tissue sealants may include fibrin, which is comprised of co-reactive thrombin and fibrinogen materials, although other multiple component materials are available. Typically, the individual components of the sealant material are stored in isolated reservoirs. When mixed, these components may coagulate very quickly, yielding a gel within a short period of time, perhaps 10 or 20 seconds. When applied to the exterior of the body, or when considerable access to the application site is possible, the rapid coagulative properties of the tissue sealant are advantageous. However, such fast-acting properties of conventional tissue sealants have presented potential problems of fouling or clogging during their application through laparoscopic devices, which typically results in the destruction of the device.

The components of the fibrin sealants used in the above-disclosed procedures are advantageously stored in separate reservoirs, such as syringes, and are only combined after delivery into the site of the incision to be sealed. Most preferably, the syringes are glass syringes due to the inertness and gas impermeability of glass. However, it is difficult to closely control the tolerances of Luer-type fittings on the nozzles of glass syringes, resulting in leakage of liquid components at the transition between the syringes and downstream adaptive components.

Separate syringes containing the co-reactive components assembled on a syringe holder are commercially available from Grifols, U.S.A. However, the axial distance between the exit nozzles of the syringes in the holder can be different from the axial distance between the inlet ports of mixing/delivery tips from other medical device suppliers.

Thus, there is a need for an adapter which fits onto the Grifols syringe holder apparatus to modify the flow path of the co-reactive materials from the axial distance between the syringe exit nozzles to the axial distance between the inlet ports of the mixing tip.

Additionally, there is a need for an adapter which can make a positive seal between inlet ports in the adapter and glass exit nozzles in the Grifols syringes.

SUMMARY

Presented herein is an adapter manifold for a multi-barrel syringe applicator, comprising an adapter body having substantially parallel inlet ports and substantially parallel exit ports, the inlet ports spaced an axial distance apart which is different from an axial distance between the exit ports, and substantially parallel syringe connectors in fluid communication with the inlet ports having Luer-type receivers on proximal ends thereof, wherein the syringe connectors are biased toward a proximal end of the adapter body.

In one form, the axial distance between the inlet ports is greater than the axial distance between the exit ports.

In other forms, the biasing is achieved with an elastomer spacer captive between the adapter manifold and the Luer-type receivers, or with springs captive between the adapter manifold and the Luer-type receivers, such as where compression springs surround the inlet ports and the syringe connectors, and are captive between annular spring seats surrounding the inlet ports and the syringe connectors.

In yet another form, the syringe connectors have cylindrical tubes on distal ends thereof, slidably positioned within the inlet ports of the adapter body, and O-rings are provided on distal portions of the cylindrical tubes sealing the syringe connectors within the inlet ports.

In one form, the Luer-type receivers of the syringe connectors are held slidably captive within the adapter body by a Luer-type retainer positioned within a proximal portion of the adapter body having substantially parallel apertures surrounding the Luer-type receivers.

In another form, the adapter manifold further comprises substantially parallel Luer-type connections distal to the exit ports.

In yet another form, the adapter manifold further comprises flexible snap hooks inside a proximal portion of the adapter body, structured and arranged to capture a mating portion of a multi-barrel syringe applicator.

Additionally presented is an adapter manifold for a dual barrel syringe applicator, comprising an adapter body having two side-by-side fluid passages therein, the fluid passages having side-by-side inlet ports spaced a first axial distance apart, and side-by-side exit ports spaced a second axial distance apart, wherein the first axial distance is different from the second axial distance, and wherein the inlet ports are surrounded by an annular spring seat, two side-by-side syringe connectors having Luer-type receivers on proximal portions thereof and cylindrical tubes on distal portions thereof, the cylindrical tubes slidably fitting into the side-by-side inlet ports, with annular spring seats surrounding the cylindrical tubes, a Luer-type retainer positioned within a proximal portion of the adapter body having side-by-side apertures surrounding the Luer-type receivers, and compression springs between the spring seats of the adapter body and the spring seats of the syringe connectors.

In one form, the first axial distance is greater than the second axial distance.

In another form, the compression springs bias the Luer-type receivers against the Luer-type retainer.

The adapter manifold can further comprise side-by-side Luer-type connections distal to and in fluid communication with the exit ports, and O-rings on distal portions of the cylindrical tubes sealing the syringe connectors within the inlet ports.

Additionally, the adapter manifold can further comprise flexible snap hooks inside a proximal portion of the adapter body, structured and arranged to capture a mating portion of a multi-barrel syringe applicator.

Also presented herein is a multi-barrel syringe delivery system for co-reactive materials, comprising a multi-barrel syringe applicator having substantially parallel syringe bodies with delivery nozzles at distal ends of the syringe bodies, a manifold comprising an adapter body having substantially parallel inlet ports and substantially parallel exit ports, the inlet ports spaced an axial distance apart which is different from an axial distance between the exit ports, the inlet ports of the manifold in fluid communication with the delivery nozzles, and a spray or drip mixing tip connected to the exit ports at a distal end of the manifold.

Advantageously, the syringe applicator has a multi-piece shell, the inner portions of which conform to the substantially parallel syringe bodies, and wherein a distal end of the multi-piece shell snap-fits into a proximal end of the adapter body.

In one form, an axial distance between the delivery nozzles is the same as the axial distance between the adapter inlet ports, and internal passages within the manifold are structured and arranged to adapt from the axial distance between the inlet ports to the axial distance between the exit ports.

In another form, the adapter body further comprises substantially parallel syringe connectors in fluid communication with the inlet ports and having Luer-type receivers on proximal ends thereof, wherein the syringe connectors are biased into a sealing communication with the syringe body delivery nozzles.

In one form, the biasing is achieved with an elastomer spacer captive between the adapter body and the Luer-type receivers. Alternatively, the biasing is achieved with springs captive between the adapter body and the Luer-type receivers, such as wherein the springs are compression springs surrounding the inlet ports and the syringe connectors, and are captive between annular spring seats surrounding the inlet ports and the syringe connectors.

In another form, the syringe connectors have cylindrical tubes on distal ends thereof, slidably positioned within the inlet ports of the adapter body.

In yet another form, the Luer-type receivers of the syringe connectors are held slidably captive within the adapter body by a Luer-type retainer positioned within a proximal portion of the adapter body having substantially parallel apertures surrounding the Luer-type receivers.

Advantageously, the multi-barrel syringe delivery system can further comprise O-rings on distal portions of the cylindrical tubes sealing the syringe connectors within the inlet ports, and flexible snap hooks inside a proximal portion of the adapter body, structured and arranged to capture a mating portion of the multi-barrel syringe applicator.

BRIEF DESCRIPTION OF THE DRAWINGS

The forms disclosed herein are illustrated by way of example, and not by way of limitation, in the figures of the accompanying drawings and in which like reference numerals refer to similar elements and in which.

DETAILED DESCRIPTION

Figure 1:
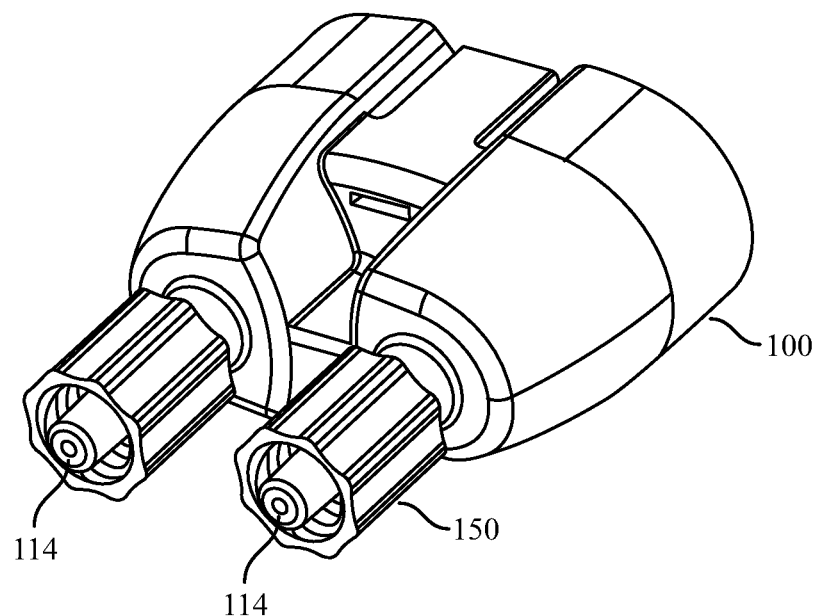
FIG. 1 is a perspective view of an adapter according to the present disclosure.
Figure 2:
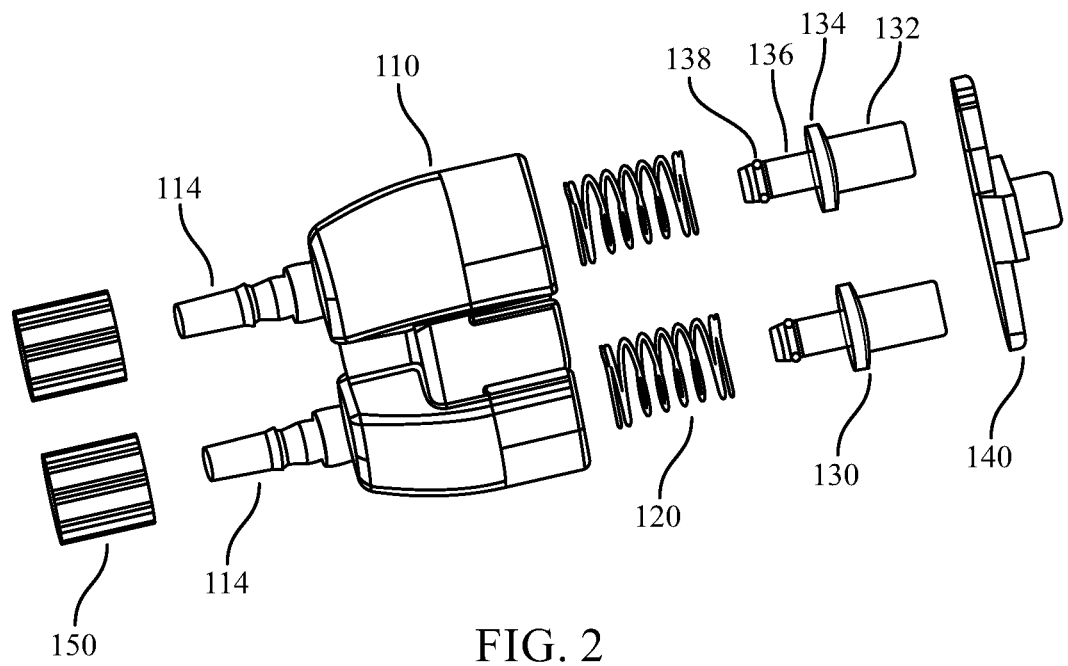
FIG. 2 is an exploded view of the adapter of FIG. 1.

Described herein is a medical device which is an adapter to connect a multi-syringe delivery device to a mixing tip, wherein the syringe nozzles of the delivery device are spaced a different axial distance apart than the inlet ports of the mixing tip.

Various aspects will now be described with reference to specific forms selected for purposes of illustration. It will be appreciated that the spirit and scope of the apparatus, system and methods disclosed herein are not limited to the selected forms. Moreover, it is to be noted that the figures provided herein are not drawn to any particular proportion or scale, and that many variations can be made to the illustrated forms.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

The term "distal" refers to that end of a device or component which is closest to the dispensing end. The term "proximal" refers to that end of a device or component which is furthest away from the dispensing end.

As used herein the term "substantially parallel" when applied to elements of the disclosed article is intended to mean that the elements are close to but not necessarily perfectly parallel. For example the elements can be disposed at slight angles relative to one another, so long as they are confined within an overlying structure in which they are disposed.

Presented herein is an adapter to connect a multi-syringe delivery device to a mixing tip for delivery of multiple co-reactive materials to a surgical site, such as an incision requiring sealing. In particular, the incision site can be one which is difficult to seal by conventional suturing, and instead requires use of a biological sealant. One well-known sealant is fibrin, which is formed when fibrinogen and thrombin are combined. While they are naturally occurring in vivo, these co-reactive materials are commercially available as isolated materials, and can be stored and delivered to medical professionals for later mixing and use in sealing incisions, wounds or the like.

Long term storage of fibrin sealant is complicated by the fact that both the polymerizable material (fibrinogen) and the initiator or accelerator (thrombin) are biological materials and are relatively labile. Long term storage is facilitated by maintaining the temperature of the materials at or below freezing (0° C.), as well as storing them in glass, well-known to be very inert and resistant to gas permeation. Fibrin adhesives containing fibrinogen and thrombin have become commercially available frozen and stored in separate glass syringe bodies, which can be packaged in a holder or cartridge, such as those disclosed in co-pending application having U.S. Ser. No. 15/957,118, now U.S. Pat. No. 10,959,714, filed on even date herewith.

Cold storage shipping is relatively expensive, and cold storage space in medical facilities can be limited. The cartridge system limits the volume of the package that needs to be in cold storage. Further, if more than one unit of biologics is needed in a procedure (as is sometimes the case), the application device can be reloaded with another cartridge rather than obtaining a new device, thus reducing waste.

The use of glass syringes to deliver these co-reactive materials to cooperating medical apparatuses, such as manifolds and mixing tips, is complicated by the fact that tolerances on the Luer-type fittings thereof are often not tight enough to prevent leakage. Additionally, manipulating glass syringes in operating theaters is difficult. Advantageously, sealing of the Luer-type tapered nozzles to other apparatuses can be accomplished with a press-fit between the glass nozzle and the corresponding receiving Luer-type taper. The presently disclosed apparatus achieves this press-fit by use of biasing means other than Luer-type nuts on the nozzles, to create a sealing force between the glass nozzles and the receiving Luer-type tapers of the accompanying apparatus (es). This system minimizes the handling of glass syringes and maximizes the ease of their preparation and use.

In some cases, the axial distance between the exit nozzles of the syringes in the cartridge can be different from the axial distance between the inlet ports of mixing/delivery tips from other medical device suppliers.

Presented herein is an adapter manifold for a multi-barrel syringe applicator to address spacing differences between the exit nozzles of multiple syringes and inlet ports of a selected mixing tip.

Figure 9:
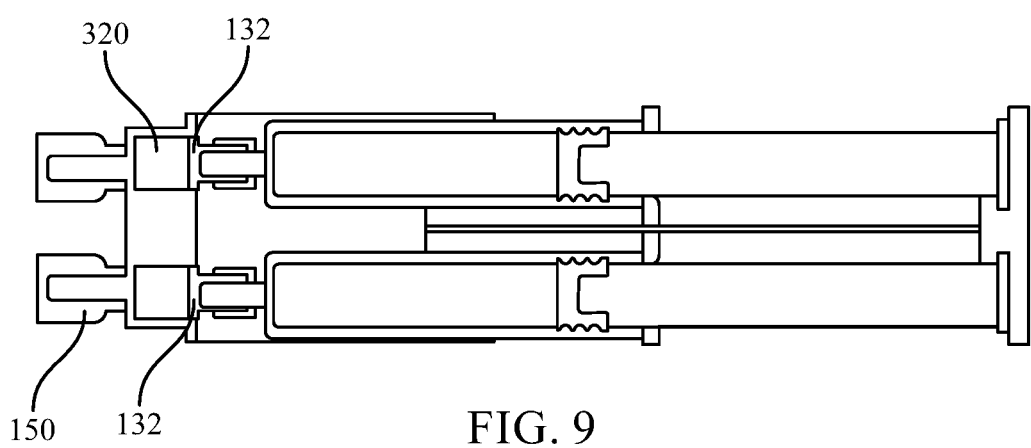
FIG. 9 is a cross-sectional schematic view of an alternative form of the syringe delivery system.

As illustrated in FIGS. 1 to 5, the adapter manifold 100 comprises an adapter body 110 having substantially parallel inlet ports 112 and substantially parallel exit ports 114, the inlet ports 112 spaced an axial distance $d_1$ apart which is different from an axial distance $d_2$ between the exit ports 114. In one form, axial distance $d_1$ is greater than axial distance $d_2$. The adapter manifold has substantially parallel syringe connectors 130 in fluid communication with the inlet ports 112, which have Luer-type receivers 132 on proximal ends thereof, and cylindrical tubes 136 on their distal ends. The cylindrical tube 136 portions of the syringe connectors 130 are slidably positioned within the inlet ports 112 of the adapter body 110, and are surrounded by biasing means, such as by compression springs 120 or an elastomer spacer 320 (FIG. 9), which act to bias the syringe connectors 130 toward a proximal end of the adapter body. Additionally, the distal portions of the cylindrical tubes 136 are provided with O-rings 138, sealing the syringe connectors 130 within the inlet ports 112. While an adaptor for a two-barrel syringe applicator is illustrated, it is understood that the adaptor can be structured and arranged to accommodate more than two syringe barrels, if desired.

Figure 3:
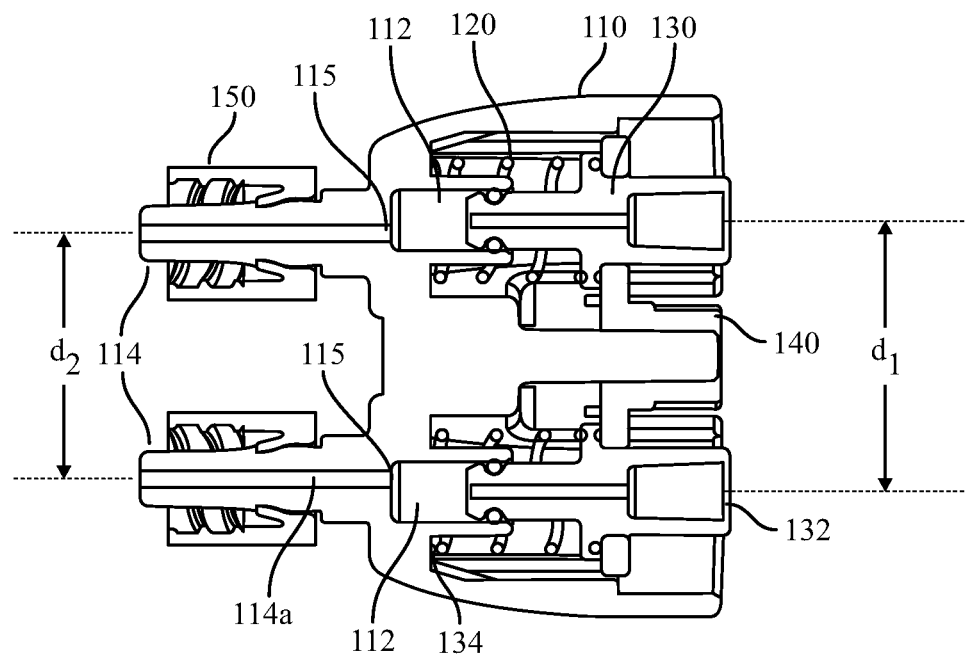
FIG. 3 is a cross-sectional top view of the adapter of FIG. 1.
Figure 4:
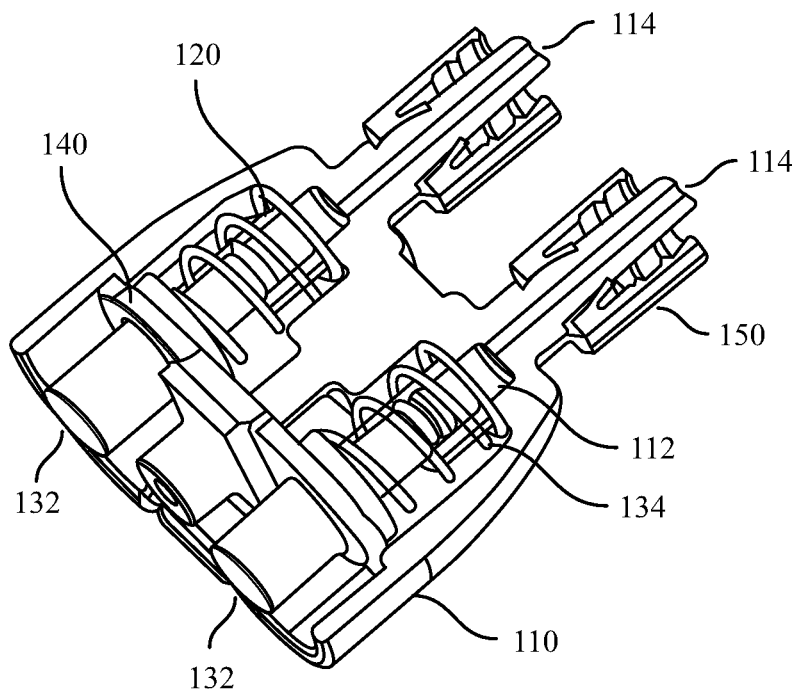
FIG. 4 is a cross-sectional perspective view of the adapter of FIG. 1 showing details of the proximal end.
Figure 5:
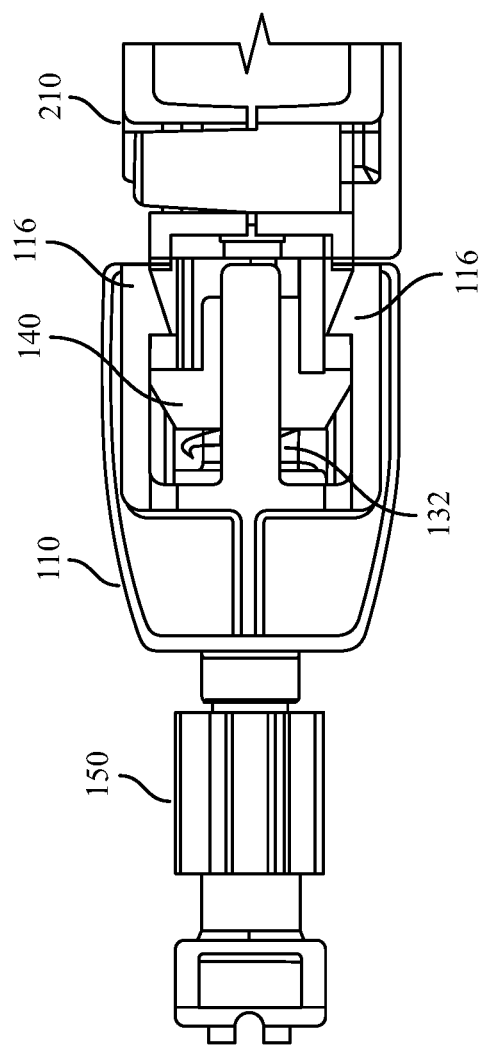
FIG. 5 is a cross-sectional side view of the adapter of FIG. 1.

The compression springs 120 surround both the inlet ports 112 and the cylindrical tubes 136 of the syringe connectors 130, and are captive between annular spring seats 134 surrounding both the inlet ports 112 and the syringe connectors 130 (best seen in FIGS. 3 and 4). Thus, when the springs 120 are compressed, the Luer-type receivers 132 of the syringe connectors 130 are biased toward the proximal end of the adaptor body 110. Biasing using the elastomer spacers 320 is similar, wherein the elastomer spacers 320 are captive between internal portions of the adapter body 110 and the Luer-type receivers 132. The Luer-type receivers 132 on the proximal ends of the syringe connectors 130 are held slidably captive within said adapter body 110 by a Luer-type retainer 140, positioned within a proximal portion of the adapter body 110. The Luer-type retainer has substantially parallel apertures which surround the Luer-type receivers 132.

Figure 6:
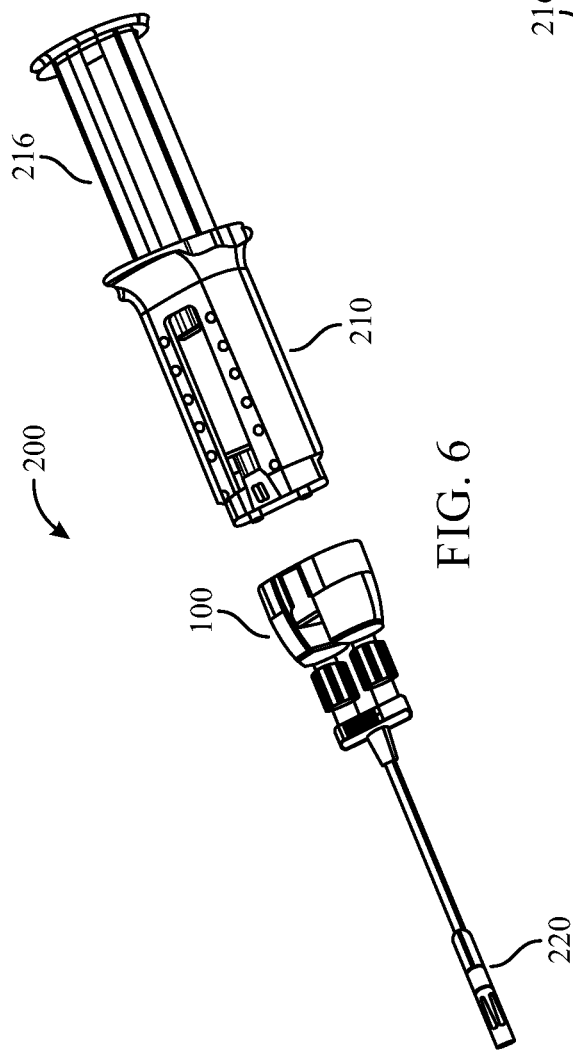
FIG. 6 is a partially exploded perspective view of the syringe delivery system according to the present disclosure.
Figure 7:
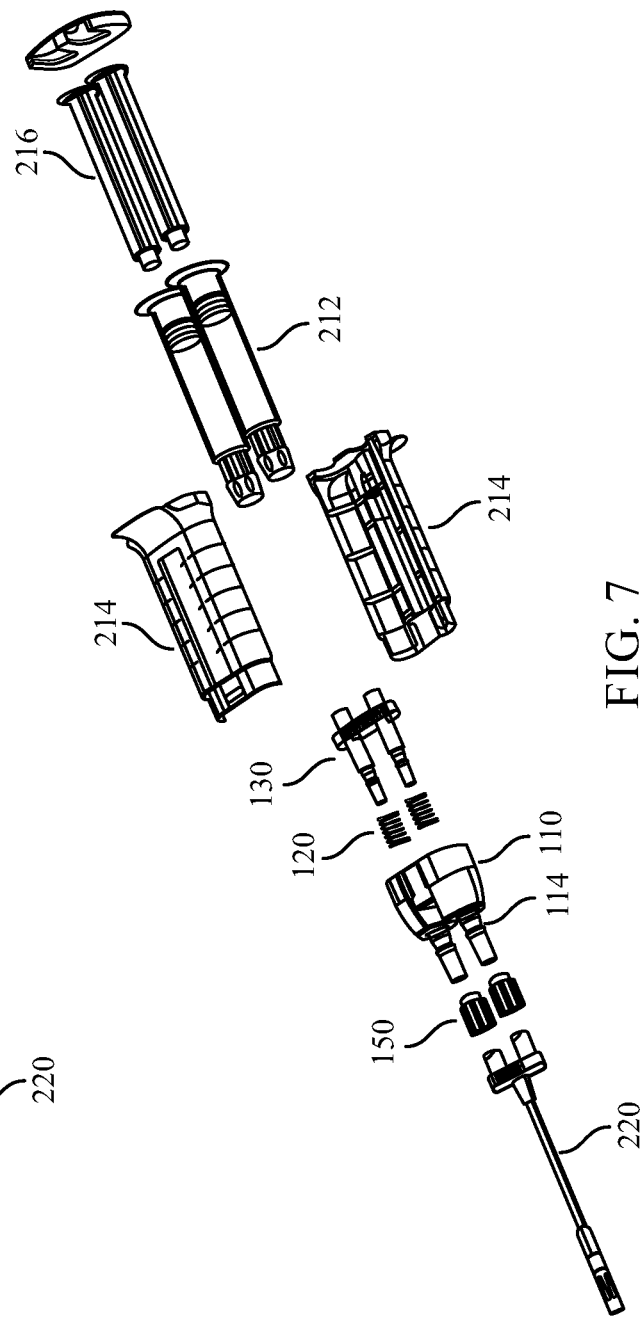
FIG. 7 is a fully exploded view of the syringe delivery system of FIG. 6.
Figure 8:
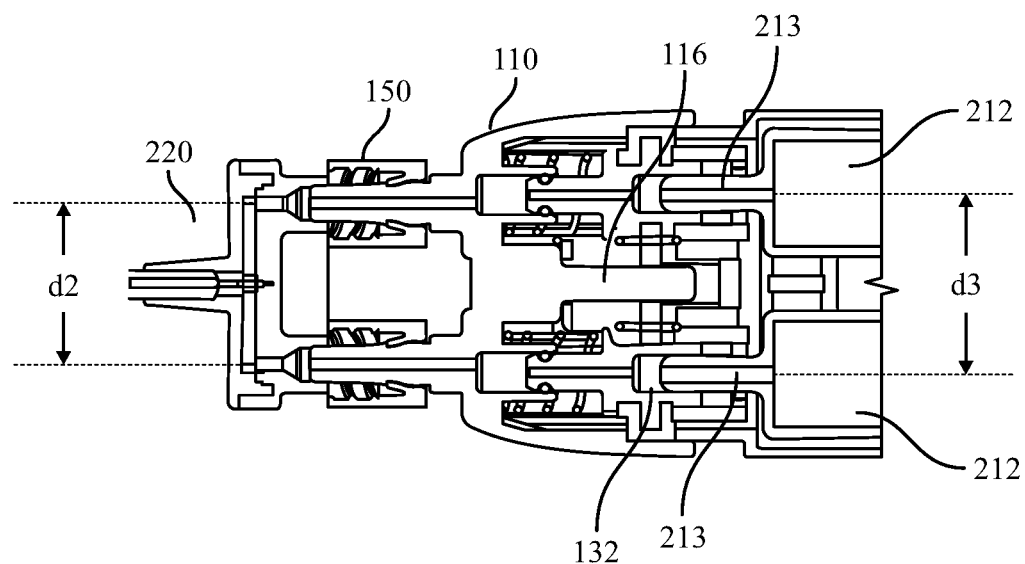
FIG. 8 is a cross-sectional top view of the adapter portion of the syringe delivery system.

The adapter manifold additionally has substantially parallel Luer-type connections 150, such as Luer-Lok® nuts, distal to the exit ports 114, to permit connection to spray mixing tips or drip mixing tips 220 (FIG. 6). The adapter also has flexible snap hooks 116 inside a proximal portion of the adapter body 110, which are structured and arranged to capture a mating portion of a multi-barrel syringe applicator 210 (FIG. 6).

In another form, presented is an adapter manifold 100 for a dual barrel syringe applicator, comprising an adapter body 110 having two side-by-side fluid passages 115 therein, the fluid passages 115 having side-by-side inlet ports 112 spaced a first axial distance $d_1$ apart, and side-by-side exit ports 114 spaced a second axial distance $d_2$ apart, wherein the first axial distance $d_1$ is different from the second axial distance $d_2$, and wherein the inlet ports 112 are surrounded by an annular spring seat 134. Tubes 114a extend from a distal portion of the inlet ports 112 and form exit ports 114. In one form, the tubes 114a have substantially parallel axes which are off-set from the center axes of the inlet ports 112 to achieve the difference in distance between $d_1$ and $d_2$. The adapter also has two side-by-side syringe connectors 130 having Luer-type receivers 132 on proximal portions thereof and cylindrical tubes 136 on distal portions thereof, the cylindrical tubes 136 slidably fitting into the side-by-side inlet ports 112, with annular spring seats 134 surrounding the cylindrical tubes 136, a Luer-type retainer 140 positioned within a proximal portion of the adapter body 110 having side-by-side apertures surrounding the Luer-type receivers 132 and compression springs 120 between the spring seats 134 of the adapter body and the spring seats 134 of the syringe connectors 136.

In another form is presented a multi-barrel syringe delivery system for delivery of co-reactive materials to a surgical site, such as an incision requiring sealing. FIGS. 6 to 9 illustrate the multi-barrel syringe delivery system 200, which includes a multi-barrel syringe applicator 210 having substantially parallel syringe bodies 212 with delivery nozzles 213 at distal ends of the syringe bodies 212. While a two-barrel syringe applicator is illustrated, it is understood that the apparatus can be structured and arranged to accommodate more than two syringe barrels, if desired. The delivery system also includes a manifold 100 comprising an adapter body 110 having substantially parallel inlet ports 112 and substantially parallel exit ports 114, the inlet ports 112 spaced an axial distance $d_1$ apart which is different from an axial distance $d_2$ between the exit ports 114 (see FIGS. 1 to 5). The inlet ports 112 of the manifold 100 are in fluid communication with the delivery nozzles 213. The delivery system also has a spray mixing tip or drip mixing tip 220 connected to the exit ports 114 at a distal end of the manifold 100.

The syringe applicator 210 has a multi-piece shell 214, the inner portions of which conform to the substantially parallel syringe bodies 212. A distal end of the multi-piece shell 214 snap-fits into a proximal end of the adapter body 110, which has snap hooks 116 inside a proximal portion thereof. In order to provide for the modification of flow paths between the syringe delivery nozzles 213 and the exit ports 114 of the adapter manifold 100, an axial distance $d_1$ between the adapter inlet ports 112 is configured to be the same as the axial distance $d_3$ between the delivery nozzles 213, and internal passages 115 within the manifold 100 are structured and arranged to adapt from the axial distance $d_1$ between the inlet ports 112 to the axial distance $d_2$ between the exit ports 114.

The adapter body 110 includes substantially parallel syringe connectors 130 in fluid communication with the inlet ports 112 and having Luer-type receivers 132 on proximal ends thereof. The syringe connectors 130 are biased into a sealing communication with the syringe body delivery nozzles 213. In one form, the biasing is achieved with an elastomer spacer 320 captive between the adapter body 110 and the Luer-type receivers 132. In another form, biasing is achieved with springs 120 captive between the adapter body 110 and the Luer-type receivers 132. Advantageously, the springs 120 are compression springs surrounding the inlet ports 112 and the syringe connectors 130, and are captive between annular spring seats 134 surrounding the inlet ports 112 and the syringe connectors 130.

In this form, the syringe connectors 130 have cylindrical tubes 136 on distal ends thereof, which are slidably positioned within said inlet ports 112 of the adapter body 110, and the Luer-type receivers 132 of the syringe connectors 130 are held slidably captive within the adapter body 110 by a Luer-type retainer 140 positioned within a proximal portion of the adapter body 110, and having side-by-side apertures surrounding the Luer-type receivers 132. Conveniently, there are O-rings 138 on distal portions of the cylindrical tubes 136, sealing the syringe connectors 130 within the inlet ports 112. Additionally, the multi-barrel syringe delivery system 200 includes flexible snap hooks 116 inside a proximal portion of the adapter body 110, which are structured and arranged to capture a mating portion of the multi-barrel syringe applicator 210.

PCT1. An adapter manifold for a multi-barrel syringe applicator, comprising an adapter body having substantially parallel inlet ports and substantially parallel exit ports, the inlet ports spaced an axial distance apart which is different from an axial distance between the exit ports, and substantially parallel syringe connectors in fluid communication with the inlet ports having Luer-type receivers on proximal ends thereof, wherein the syringe connectors are biased toward a proximal end of the adapter body.

PCT2. The adapter manifold of paragraph PCT1, wherein the axial distance between the inlet ports is greater than the axial distance between the exit ports.

PCT3. The adapter manifold of paragraph PCT1, wherein the biasing is achieved with an elastomer spacer captive between the adapter manifold and the Luer-type receivers, or with springs captive between the adapter manifold and the Luer-type receivers.

PCT4. The adapter manifold of paragraph PCT3, wherein the springs are compression springs surrounding the inlet ports and the syringe connectors, and are captive between annular spring seats surrounding the inlet ports and the syringe connectors.

PCT5. The adapter manifold of any of paragraphs PCT1 to PCT4, wherein said syringe connectors have cylindrical tubes on distal ends thereof, slidably positioned within said inlet ports of the adapter body.

PCT6. The adapter manifold of any of paragraphs PCT1 to PCT5, wherein the Luer-type receivers of the syringe connectors are held slidably captive within said adapter body by a Luer-type retainer positioned within a proximal portion of the adapter body, having substantially parallel apertures surrounding the Luer-type receivers.

PCT7. The adapter manifold of any preceding PCT paragraph, further comprising substantially parallel Luer-type connections distal to the exit ports.

PCT8. The adapter manifold of paragraph PCT5, further comprising O-rings on distal portions of the cylindrical tubes sealing the syringe connectors within the inlet ports.

PCT9. The adapter manifold of any preceding PCT paragraph, further comprising flexible snap hooks inside a proximal portion of the adapter body, structured and arranged to capture a mating portion of a multi-barrel syringe applicator.

PCT10. A multi-barrel syringe delivery system for co-reactive materials, comprising a multi-barrel syringe applicator having substantially parallel syringe bodies with delivery nozzles at distal ends of said syringe bodies; a manifold comprising an adapter body having substantially parallel inlet ports and substantially parallel exit ports, the inlet ports spaced an axial distance apart which is different from an axial distance between the exit ports, the inlet ports of said manifold in fluid communication with said delivery nozzles; and a spray or drip mixing tip connected to the exit ports at a distal end of the manifold.

PCT11. The multi-barrel syringe delivery system of paragraph PCT10, wherein the syringe applicator has a multi-piece shell, the inner portions of which conform to the substantially parallel syringe bodies, and wherein a distal end of the multi-piece shell snap-fits into a proximal end of the adapter body.

PCT12. The multi-barrel syringe delivery system of PCT10 or PCT11, wherein an axial distance between the delivery nozzles is the same as the axial distance between said adapter inlet ports, and internal passages within said manifold are structured and arranged to adapt from said axial distance between said inlet ports to said axial distance between said exit ports.

PCT13. The multi-barrel syringe delivery system of any of paragraphs PCT10 to PCT12, said adapter body further comprising substantially parallel syringe connectors in fluid communication with the inlet ports and having Luer-type receivers on proximal ends thereof, wherein the syringe connectors are biased into a sealing communication with said syringe body delivery nozzles.

PCT14. The multi-barrel syringe delivery system of paragraph PCT13, wherein the biasing is achieved with an elastomer spacer captive between the adapter body and the Luer-type receivers, or with springs captive between the adapter body and the Luer-type receivers.

PCT15. The multi-barrel syringe delivery system of paragraph PCT14, wherein the springs are compression springs surrounding the inlet ports and the syringe connectors, and are captive between annular spring seats surrounding the inlet ports and the syringe connectors.

PCT16. The multi-barrel syringe delivery system of any of paragraphs PCT13 to PCT15, wherein said syringe connectors have cylindrical tubes on distal ends thereof, slidably positioned within said inlet ports of the adapter body.

PCT17. The multi-barrel syringe delivery system of any of paragraphs PCT13 to PCT16, wherein the Luer-type receivers of the syringe connectors are held slidably captive within said adapter body by a Luer-type retainer positioned within a proximal portion of the adapter body having substantially parallel apertures surrounding the Luer-type receivers.

PCT18. The multi-barrel syringe delivery system of paragraph PCT16 or PCT17, further comprising O-rings on distal portions of the cylindrical tubes sealing the syringe connectors within the inlet ports.

PCT19. The multi-barrel syringe delivery system of any of paragraphs PCT10 to PCT18, further comprising flexible snap hooks inside a proximal portion of the adapter body, structured and arranged to capture a mating portion of the multi-barrel syringe applicator.

INDUSTRIAL APPLICABILITY

The systems and methods disclosed herein are applicable to the medical device industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and sub-combinations that are directed to one of the disclosed inventions and are novel and non-obvious. Inventions embodied in other combinations and sub-combinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

What is claimed:

1. An adapter manifold for a multi-barrel syringe applicator, comprising:
    an adapter body having substantially parallel inlet ports, substantially parallel exit ports and substantially parallel Luer-type connections, the inlet ports spaced an axial distance apart which is different from an axial distance between the exit ports, and substantially parallel syringe connectors in fluid communication with the inlet ports having Luer-type receivers on proximal ends thereof, wherein the syringe connectors are biased toward a proximal end of the adapter body by compression springs surrounding the inlet ports and the syringe connectors, captive between annular spring seats surrounding the inlet ports and the syringe connectors.

2. The adapter manifold of claim 1, wherein the axial distance between the inlet ports is greater than the axial distance between the exit ports.

3. The adapter manifold of claim 1, wherein said syringe connectors have cylindrical tubes on distal ends thereof, slidably positioned within said inlet ports of the adapter body.

4. The adapter manifold of claim 3, further comprising O-rings on distal portions of the cylindrical tubes sealing the syringe connectors within the inlet ports.

5. The adapter manifold of claim 1, wherein the Luer-type receivers of the syringe connectors are held slidably captive within said adapter body by a Luer-type retainer positioned within a proximal portion of the adapter body having substantially parallel apertures surrounding the Luer-type receivers.

6. The adapter manifold of claim 1, further comprising flexible snap hooks inside a proximal portion of the adapter body, structured and arranged to capture a mating portion of the multi-barrel syringe applicator.

7. An adapter manifold for a dual barrel syringe applicator, comprising:
    an adapter body having two side-by-side fluid passages therein, said fluid passages having side-by-side inlet ports spaced a first axial distance apart, side-by-side exit ports spaced a second axial distance apart and substantially parallel Luer-type connections, wherein the first axial distance is different from the second axial distance, and wherein the inlet ports are surrounded by annular spring seats;

two side-by-side syringe connectors having Luer-type receivers on proximal portions thereof and cylindrical tubes on distal portions thereof, said cylindrical tubes slidably fitting into said side-by-side inlet ports, with annular spring seats surrounding the cylindrical tubes;

a Luer-type retainer positioned within a proximal portion of the adapter body having side-by-side apertures surrounding the Luer-type receivers; and compression springs between the spring seats of the adapter body and the spring seats of the syringe connectors.

8. The adapter manifold of claim 7, wherein the first axial distance is greater than the second axial distance.

9. The adapter manifold of claim 7, wherein the compression springs bias the Luer-type receivers against the Luer-type retainer.

10. The adapter manifold of claim 7, further comprising O-rings on distal portions of the cylindrical tubes sealing the syringe connectors within the inlet ports.

11. The adapter manifold of claim 7, further comprising flexible snap hooks inside the proximal portion of the adapter body, structured and arranged to capture a mating portion of the dual barrel syringe applicator.

12. A multi-barrel syringe delivery system for co-reactive materials, comprising:
a multi-barrel syringe applicator having substantially parallel syringe bodies with delivery nozzles at distal ends of said syringe bodies;
a manifold comprising an adapter body having substantially parallel inlet ports and substantially parallel exit ports, the inlet ports spaced an axial distance apart which is different from an axial distance between the exit ports, the inlet ports of said manifold in fluid communication with said delivery nozzles, and substantially parallel syringe connectors in fluid communication with the inlet ports and having Luer-type receivers on proximal ends thereof, wherein the syringe connectors are biased into a sealing communication with said delivery nozzles of said syringe bodies with compression springs captive between the adapter body and the Luer-type receivers; and
a spray or drip mixing tip connected to the exit ports at a distal end of the manifold.

13. The multi-barrel syringe delivery system of claim 12, wherein the syringe applicator has a multi-piece shell having inner portions which conform to the substantially parallel syringe bodies, and wherein a distal end of the multi-piece shell snap-fits into a proximal end of the adapter body.

14. The multi-barrel syringe delivery system of claim 12, wherein an axial distance between the delivery nozzles is the same as the axial distance between said inlet ports, and internal passages within said manifold are structured and arranged to adapt from said axial distance between said inlet ports to said axial distance between said exit ports.

15. The multi-barrel syringe delivery system of claim 12, wherein said syringe connectors have cylindrical tubes on distal ends thereof, slidably positioned within said inlet ports of the adapter body.

16. The multi-barrel syringe delivery system of claim 12, wherein the Luer-type receivers of the syringe connectors are held slidably captive within said adapter body by a Luer-type retainer positioned within a proximal portion of the adapter body having substantially parallel apertures surrounding the Luer-type receivers.

17. The multi-barrel syringe delivery system of claim 12, further comprising O-rings on distal portions of cylindrical tubes sealing the syringe connectors within the inlet ports.

18. The multi-barrel syringe delivery system of claim 12, further comprising flexible snap hooks inside a proximal portion of the adapter body, structured and arranged to capture a mating portion of the multi-barrel syringe applicator.

19. An adapter manifold for a multi-barrel syringe applicator, comprising:
an adapter body having substantially parallel inlet ports and substantially parallel exit ports, the inlet ports spaced an axial distance apart which is different from an axial distance between the exit ports and substantially parallel Luer-type connections, and substantially parallel syringe connectors in fluid communication with the inlet ports having Luer-type receivers on proximal ends thereof and cylindrical tubes on distal ends thereof, slidably positioned within said inlet ports of the adapter body and having O-rings on distal portions of the cylindrical tubes sealing the syringe connectors within the inlet ports, wherein the syringe connectors are biased toward a proximal end of the adapter body.

20. The adapter manifold of claim 19, wherein the axial distance between the inlet ports is greater than the axial distance between the exit ports.

21. The adapter manifold of claim 20, wherein the biasing is achieved with springs captive between the adapter body and the Luer-type receivers.

22. The adapter manifold of claim 21, wherein the springs are compression springs surrounding the inlet ports and the syringe connectors and are captive between annular spring seats surrounding the inlet ports and the syringe connectors.

23. The adapter manifold of claim 19, wherein the biasing is achieved with an elastomer spacer captive between the adapter body and the Luer-type receivers.

24. The adapter manifold of claim 23, further comprising flexible snap hooks inside a proximal portion of the adapter body, structured and arranged to capture a mating portion of the multi-barrel syringe applicator.

25. The adapter manifold of claim 19, wherein the Luer-type receivers of the syringe connectors are held slidably captive within said adapter body by a Luer-type retainer positioned within a proximal portion of the adapter body having substantially parallel apertures surrounding the Luer-type receivers.

26. A multi-barrel syringe delivery system for co-reactive materials, comprising:
a multi-barrel syringe applicator having substantially parallel syringe bodies with delivery nozzles at distal ends of said syringe bodies;
a manifold comprising an adapter body having substantially parallel inlet ports and substantially parallel exit ports, the inlet ports spaced an axial distance apart which is different from an axial distance between the exit ports, the inlet ports of said manifold in fluid communication with said delivery nozzles;
said adapter body further comprising substantially parallel syringe connectors in fluid communication with the inlet ports and having Luer-type receivers on proximal ends thereof, wherein the syringe connectors are biased into a sealing communication with said delivery nozzles of said syringe bodies;
said syringe connectors having cylindrical tubes on distal ends thereof, slidably positioned within said inlet ports of the adapter body and having O-rings on distal portions of the cylindrical tubes sealing the syringe connectors within the inlet ports; and a spray or drip mixing tip connected to the exit ports at a distal end of the manifold.

27. The multi-barrel syringe delivery system of claim 26, wherein the syringe applicator has a multi-piece shell having inner portions which conform to the substantially parallel syringe bodies, and wherein a distal end of the multi-piece shell snap-fits into a proximal end of the adapter body.

28. The multi-barrel syringe delivery system of claim 26, wherein an axial distance between the delivery nozzles is the same as the axial distance between said inlet ports, and internal passages within said manifold are structured and arranged to adapt from said axial distance between said inlet ports to said axial distance between said exit ports.

29. The multi-barrel syringe delivery system of claim 26, wherein the biasing is achieved with an elastomer spacer captive between the adapter body and the Luer-type receivers.

30. The multi-barrel syringe delivery system of claim 26, wherein the biasing is achieved with springs captive between the adapter body and the Luer-type receivers.

31. The multi-barrel syringe delivery system of claim 30, wherein the springs are compression springs surrounding the inlet ports and the syringe connectors and are captive between annular spring seats surrounding the inlet ports and the syringe connectors.

32. The multi-barrel syringe delivery system of claim 26, wherein the Luer-type receivers of the syringe connectors are held slidably captive within said adapter body by a Luer-type retainer positioned within a proximal portion of the adapter body having substantially parallel apertures surrounding the Luer-type receivers.

\* \* \* \* \*